(12) United States Patent
Scheckel et al.

(10) Patent No.: US 10,478,538 B2
(45) Date of Patent: Nov. 19, 2019

(54) FLEXIBLE CATHETER WITH A DRIVE SHAFT

(71) Applicant: ECP ENTWICKLUNGSGESELLSCHAFT MBH, Berlin (DE)

(72) Inventors: Mario Scheckel, Berlin (DE); Joerg Schumacher, Teltow (DE)

(73) Assignee: ECP ENTWICKLUNGSGESELLSCHAFT MBH, BerlinAmtsgericht Berlin (Charlottenburg) (DE)

( * ) Notice: Subject to any disclaimer, the term of this patent is extended or adjusted under 35 U.S.C. 154(b) by 114 days.

(21) Appl. No.: 15/033,443

(22) PCT Filed: Oct. 31, 2014

(86) PCT No.: PCT/EP2014/073504
§ 371 (c)(1),
(2) Date: Apr. 29, 2016

(87) PCT Pub. No.: WO2015/063281
PCT Pub. Date: May 7, 2015

(65) Prior Publication Data
US 2016/0256620 A1 Sep. 8, 2016

(30) Foreign Application Priority Data

Nov. 1, 2013 (EP) .................................... 13191307

(51) Int. Cl.
*A61M 1/10* (2006.01)
(52) U.S. Cl.
CPC ........ *A61M 1/1008* (2014.02); *A61M 1/1029* (2014.02); *A61M 1/1031* (2014.02); *A61M 1/1017* (2014.02)

(58) Field of Classification Search
CPC ..... A61M 1/008; A61M 1/029; A61M 1/1031
See application file for complete search history.

(56) References Cited

U.S. PATENT DOCUMENTS

| 6,685,696 B2 | 2/2004 | Fleischhacker et al. |
| 8,540,695 B2 | 9/2013 | Shimogami et al. |
| (Continued) | | |

FOREIGN PATENT DOCUMENTS

| CN | 1524000 A1 | 8/2004 |
| CN | 102245254 A1 | 11/2011 |
| (Continued) | | |

OTHER PUBLICATIONS

Anonymous: "H.C. Starck—Product Information MP35N Nickel/Cobalt/Chromium Molybdenum Alloy", retrieved from internet: URL:http//web/archive.org/web/20131002073855/http://www.hcstarck.com/mp35n_molybdenum (3 pages) Oct. 2013.
(Continued)

*Primary Examiner* — Paula J Stice
(74) *Attorney, Agent, or Firm* — White & Case LLP

(57) ABSTRACT

The invention relates to a flexible catheter (1) with a drive shaft (2), with a sleeve (6) surrounding the drive shaft (2) and with a sheath (7) surrounding the drive shaft (2) and the sleeve (6), wherein the drive shaft, the sleeve (6) and the sheath (7) are pliable, wherein the drive shaft (2) at a proximal end of the drive shaft (2) comprises a coupling element (5) for connecting the drive shaft (2) to a drive motor (18), wherein the drive shaft (2) at least regionally consist of a alloy which contains at least 10% by weight of chromium, nickel and cobalt in each case. The invention moreover relates to a blood pump arrangement with such a catheter.

39 Claims, 9 Drawing Sheets

(56) References Cited

U.S. PATENT DOCUMENTS

Figure 1:
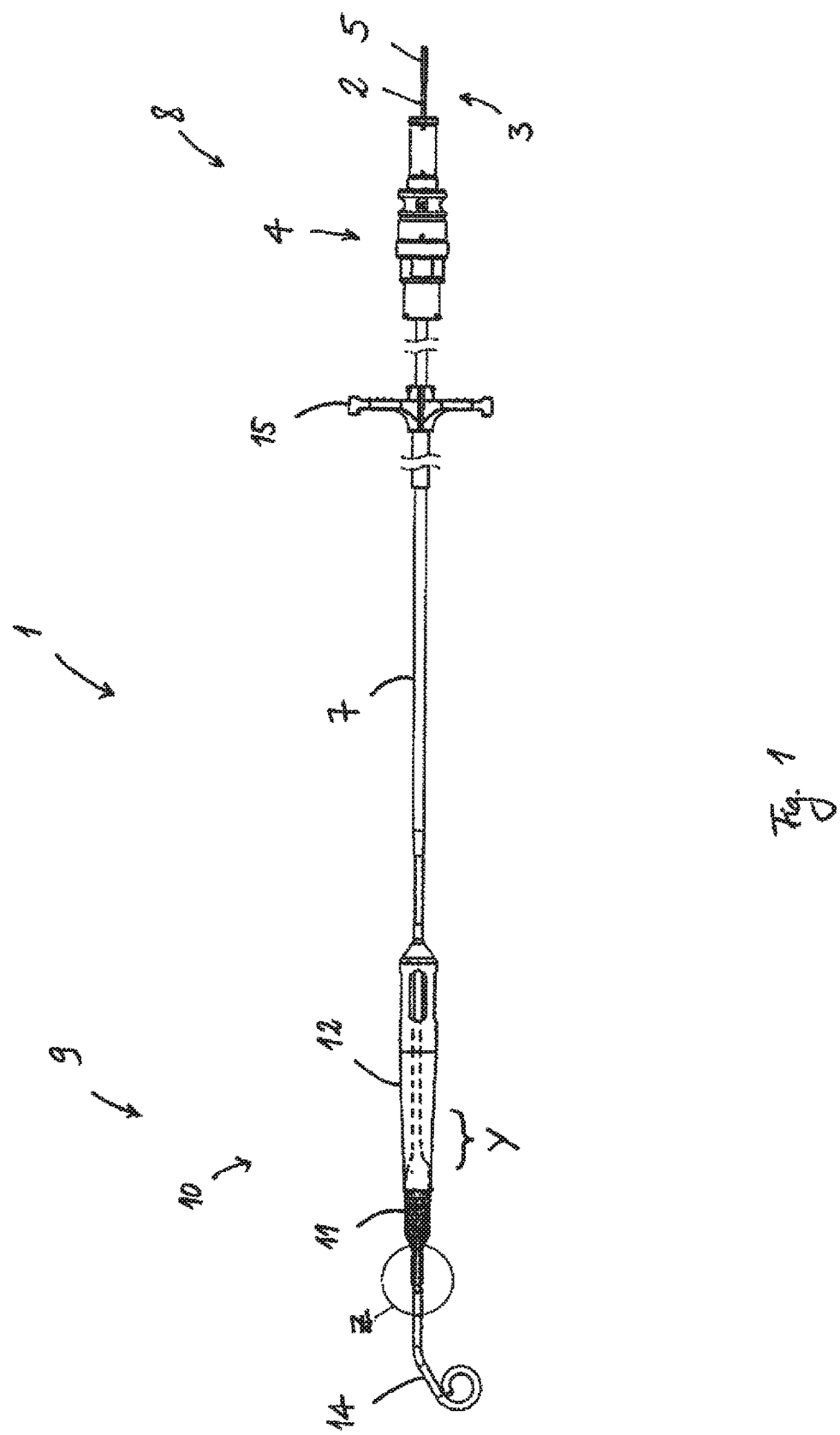

| | | | |
|---|---|---|---|
| 2008/0306327 A1 | 12/2008 | Schifflette | |
| 2009/0093764 A1* | 4/2009 | Pfeffer | A61M 1/1031 604/151 |
| 2012/0089225 A1 | 4/2012 | Akkerman et al. | |
| 2012/0178986 A1* | 7/2012 | Campbell | A61M 1/1034 600/16 |
| 2013/0102834 A1 | 4/2013 | Kaneshima et al. | |
| 2014/0200664 A1 | 7/2014 | Akkerman et al. | |
| 2015/0045695 A1* | 2/2015 | Simpson | A61L 31/022 600/585 |
| 2015/0125505 A1* | 5/2015 | Wustenberg | A61K 9/1611 424/422 |

FOREIGN PATENT DOCUMENTS

| | | |
|---|---|---|
| CN | 102933253 A1 | 2/2013 |
| EP | 2314330 A1 | 4/2011 |
| WO | WO-99/34121 A1 | 7/1999 |
| WO | WO-2008/151236 A2 | 12/2008 |

OTHER PUBLICATIONS

International Search Report, PCT/EP2014/073504, dated Jan. 21, 2015 with English translation of ISR (16 pages).

\* cited by examiner

| Kaltverfestigungs-grad %CW | Fließgrenze (Yield Strength) KSI | MPa | Zugfestigkeit (Ultimate Tensile Strength) KSI | MPa | Bruchdehnung (Elongation) % |
|---|---|---|---|---|---|
| 0 | 130 | 896 | 190 | 1310 | 40,00 |
| 20 | 190 | 1310 | 240 | 1655 | 8,00 |
| 37 | 240 | 1655 | 280 | 1931 | 3,80 |
| 50 | 270 | 1862 | 300 | 2068 | 3,80 |
| 60 | 290 | 1999 | 320 | 2206 | 3,50 |
| 68 | 300 | 2068 | 330 | 2275 | 3,50 |
| 75 | 305 | 2103 | 340 | 2344 | 3,30 |
| 80 | 315 | 2172 | 350 | 2413 | 3,00 |
| 84 | 325 | 2241 | 360 | 2482 | 3,00 |
| 90 | 333 | 2296 | 370 | 2551 | 3,00 |
| 93 | 338 | 2330 | 375 | 2586 | 2,50 |
| 95 | 340 | 2344 | 380 | 2620 | 2,50 |

FLEXIBLE CATHETER WITH A DRIVE SHAFT

CROSS-REFERENCE TO RELATED APPLICATIONS

This application is a United States National Stage filing under 35 U.S.C. § 371 of International Application No. PCT/EP2014/073504, filed Oct. 31, 2014, which claims priority to European Patent Application No. 13191307.1, filed Nov. 1, 2013, the contents of both of which are incorporated by reference herein in their entirety. International Application No. PCT/EP2014/073504 was published under PCT Article 21(2) in German.

The invention relates to a flexible catheter with a pliable drive shaft, according to the preamble of the main claim, as well as to a blood pump arrangement with such a catheter.

Such catheters are typically used, within a body of a human or animal, to produce or transmit a torque or rotation movement. The drive shaft runs axially along the longitudinal extension of the catheter between a proximal end of the catheter and a distance end of the catheter. Typically, a proximal end of the drive shaft is connected outside the body to a drive motor, in order to produce the torque or the rotation movement and to transmit it onto the drive shaft. A rotation element or functional element which is designed according to the respective application is connected to the drive shaft in a rotational fixed manner, at the distal end of the drive shaft. With regard to the functional element, it can be the case for example of a milling cutter, a rotor ablator or a pump rotor for delivering blood.

For many applications, it is necessary to lead the catheter along a desired path through the body, for example along or within blood vessels, in order to position the distal end of the catheter at a desired location within the body, for example within a heart ventricle, for the duration of the respective application. Apart from the pliability and flexibility which is necessary for this, as a rule yet further criteria must be fulfilled. For example, in some applications, it is necessary for rotation movements to be produced or transmitted by the drive shaft at a very high rotation speed, for example the necessary rotation speed can be more than 10,000, more that 20,000 or even more than 30,000 revolutions per minute, such as in the already mentioned case of delivering blood for example. Moreover, particularly high demands are placed on the mechanical and the chemical loadability of the catheter, particularly at the drive shaft, in cases, in which the rotation movement must be produced over a longer period of time, thus for several hours, days or even weeks, as is can likewise when delivering (pumping) blood. Material fatigue and damaging processes on the drive shaft and on other components of the catheter should only progress as slowly as possible, and moreover as predictably and as controllably as possible. Tearing and breakage of the drive shaft on operation should be able to be ruled out with an as large as possible certainty in critical applications, such as when delivering blood. Hereby, it is not favourable if the flexible drive shaft is operated in a sheath which is too hard and which wears the shaft.

On the other hand, should a failure of the shaft occur despite this, then it must be ensured with the greatest possible certainly that the ends of the shaft which are thereby typically splayed open, do not work through the sheath of the catheter usually consisting of plastics, at high speed. The ends of the shaft would freely rotate in the blood vessel in such a case.

It is thus the object of the present invention, to suggest a flexible catheter with a pliable drive shaft and which is as reliable is possible and is also suited as much as possible for a permanent operation at high speeds. A blood pump arrangement is moreover suggested, which is likewise as reliable as possible and is as suited as much as possible also for the permanent operation at high speeds.

This object is achieved by a catheter according to the main claim, as well as by a catheter and a blood pump arrangement according to the auxiliary claims. Preferred embodiments and further developments are to be deduced from the dependent claims.

As is described hereinafter in a detailed manner, this patent application discloses several aspects, wherein each of these aspects is a part of a coherent invention. On the other hand, each of the aspects also per se already represents an autonomous invention. The aspects can therefore be realised independently of one another (and in each case taken by themselves represent special further developments of a generic catheter according to the preamble of the main claim) and can moreover be infinitely combined with one another, in order to synergistically improve a generic catheter or a blood pump arrangement with a generic catheter. Thus for example a generic catheter can be designed according to one of these aspects and can simultaneously also be designed according to one (or more) further aspect(s). This catheter is then a particularly advantageous embodiment of a catheter according to the first mentioned aspect. Each of the aspects thus also permits a further development of each other aspect.

The first of these aspects relates to the material or the material characteristics of the drive shaft, the second aspect to the geometric design of the drive shaft, the third aspect to the design of the sleeve, the fourth aspect to the connection between the drive shaft and the drive motor, the fifth aspect to the mounting of the drive shaft and the sixth aspect to a lubricant for the drive shaft. Each of these aspects contributes to the improvement of the loadability and the reliability of the catheter or of the blood pump arrangement.

A generic flexible catheter accordingly comprises a drive shaft, a sleeve surrounding the drive shaft and a sheath surrounding the drive shaft and the sleeve, wherein the drive shaft, the sleeve and the sheath are pliable. The drive shaft at a proximal end of the drive shaft comprises a coupling element or a coupling head, for the connection of the drive shaft to the drive motor.

Typically, the (axial) total length of the catheter is between 50 cm and 200 cm, and as a rule the total length lies in a region between 80 cm and 150 cm. Typically, the (axial) total lengths of the drive shaft, the sleeve and the sheath likewise lie within of one these regions in each case. The flexibility or the pliability of the catheter, thus in particular of the drive shaft, the sleeve and the sheath, should be sufficient, in order to be able to elastically bend the catheter with a radius of curvature in a region between 20 mm and 40 mm, preferably in a region between 25 mm and 35 mm, in particular of about 30 mm. With such a curvature, in particular the drive shaft rotating at an operational speed and the sleeve, where possible, should deform only elastically, thus if possible, no permanent (plastic) deformations or changes of the drive shaft or the sleeve should occur. In particular such an elastic curvature with the mentioned radius of curvature should also be possible with a roughly U-shaped curvature of the catheter of about 180°, with which the catheter therefore is continuously curved, for example along an axial section of the catheter with a length of about 80 mm to 150 mm, typically 100 mm to 120 mm (depending on the radius of curvature). Such curvatures of the catheter occur for example if the catheter runs through the aortic arch into the left ventricle. Moreover, a rhythmic change of the described radius of curvature typically occurs due to the rhythmic heart action, wherein the position of the curvature with respect to the catheter can also rhythmically change.

In many cases, it is not necessary for the catheter to have such a flexibility along its entire axial longitudinal extension. It can already be sufficient for this to be given in a certain axial section (or several axial sections). Often, at least a distal end-piece or a distal part-piece of the catheter has such a flexibility, as in the case of delivering blood, for example if a distal end of the catheter has to be placed in a ventricle. This distal end-piece or part-piece for example can have an axial length in one of the length regions mentioned above.

As is described in more detail further below, the pliability and flexibility of the catheter or the drive shaft also cannot be too large in some cases, in particular in those axial sections of the drive shaft, which run distally or proximally outside the sleeve or exit out of the sleeve, so that a regional stiffening of the drive shaft to a certain extent is advantageous in at least one of these sections, or, depending on the demands of the respective application, can even be necessary. A minimisation of the vibration can advantageously be achieved by such stiffening, by which means the risk of a haemolysis can also be reduced.

According to the first aspect of the invention, the drive shaft of the catheter can consist completely or at least regionally of an alloy which in each case contains at least 10% by weight of chromium, nickel and cobalt. The alloy preferably contains at least 30% by weight of nickel, preferably however not more than 40% by weight of nickel. The alloy preferably contains at least 30% by weight of cobalt, preferably however not more than 40% by weight of cobalt. The alloy preferably contains at least 15% by weight of chromium, preferably however not more than 25% by weight of chromium. The alloy preferably also contains molybdenum, preferably at least 5% by weight, preferably however not more than 15% by weight of molybdenum.

The alloy for example as alloy components can comprise about 35% by weight of nickel, about 35% by weight of cobalt, about 20% by weight of chromium and about 10% by weight of molybdenum. These alloy components of the alloy in each case can be larger or smaller by up to 3% by weight, or larger or smaller by in each case up to 2% by weight. The alloy components of these elements can correspond to the alloy components of these elements in the alloy MP35N® or the alloy components of these elements in the alloy 35 NLT® or differ from this in each case by up to 2% by weight higher or lower, or from this in each case by up to 1% higher or lower. The alloy can moreover contain further alloy elements. These can be selected and weighted according to those of the alloy MP35N® or those of the alloy 35NLT®.

Preferably, with regard to the alloy it is the case of MP35N® or 35NLT®, or is manufactured in a corresponding (or the same) manner, i.e. with corresponding (or the same) method steps and with corresponding (or the same) method parameters as MP35NO or as 35 NLT®. For example, one can envisage the alloy of the drive shaft or the drive shaft as a whole being work-hardened or being manufactured or formed by way of applying (high) cold-forming or work-hardening. A work-hardening degree of the material of the drive shaft and/or of the sleeve for example is between 35% and 70% and/or between 40% and 60%. A tensile strength of the material in a region between 1900 MPa and 2200 MPa can result from this.

Figures 15, 16:
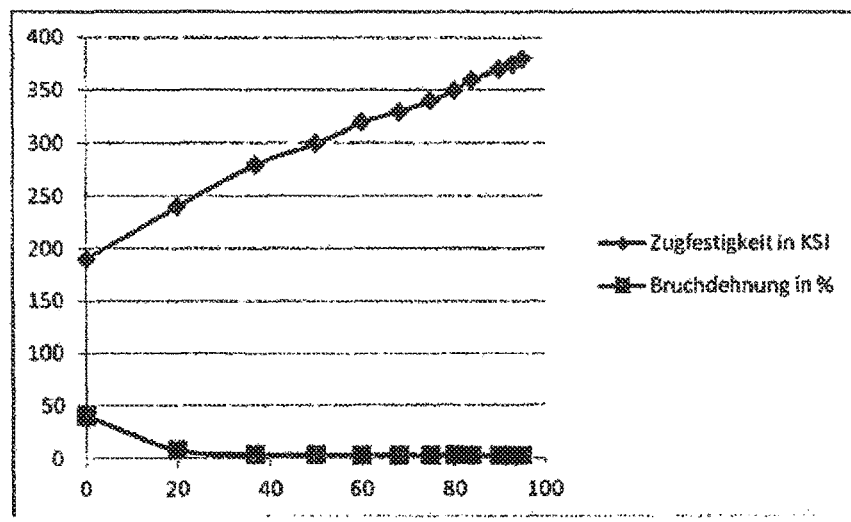

The relations between the yield point, tensile strength, elongation at break and work-hardening degree with the example of the material 35NLT is represented by way of example in FIGS. 16 and 17 (based on the details of the manufacturer Fort Wayne Metals). With this example, it is shown that different heat-treatment conditions and work-hardening degrees of a material can generally lead to very different material characteristics. Often, these are only found to be unsuitable for a flexible drive shaft with the benefit of hindsight.

A high work-hardening for example is not uncritical, since this can lead to a reduction of the maximal elongation at break as well as the toughness of the material. The reverse bending strength of the drive shaft as well as the achievable bending radius of the shaft can be negatively influenced by way of this. On the other hand, a low work-hardening entails a relative low harness and tensile strength of the material. A hardness which is to low has a direct influence on the wearing behaviour of the shaft and thus on its endurance strength, and for example can result in an increased wear and abrasion on operation. This is particularly critical in the case of a sliding/friction pairing, as is typical for flexible shafts. A reduced tensile strength results in a low reverse bending strength.

The optimisation of a stable and durable flexible drive shaft is highly complex since different optimisation targets of the drive shaft entail diverging material characteristics, so that no standardised and meaningfully applicable optimisation method or evident parameter window result for this.

However, it has been surprisingly found that drive shafts which consist completely or at least regionally of a material which has a tensile strength in a region between 1800 N/mm$^2$ and 2400 N/mm$^2$, preferably from 2034 to 2241 N/mm$^2$ (thus from 295 KSI to 325 KSI), lead to good results. In particular, with regard to the material, it can be the case of one of the alloys described here, thus one which comprises at least 10% by weight of chromium, nickel and cobalt in each case. However, other materials are also considered for the drive shaft, apart from these alloys, such as for example metallic and non-metallic materials, in particular also plastics and composite materials.

A drive shaft which consists completely or at least regionally of such an alloy or such a material is also suitable for applications at a very high speeds and a long permanent operation, so that it is also possible to maintain the initially mentioned speed regions for a longer time duration with such a drive shaft. The torques, which transmit such high rotation speed by way of the drive shaft however are typically relatively low, in particular when delivering blood, wherein the torque for the drive of an expanded pump rotor is typically larger due to the larger diameter. Even if the application of the alloys MP35N® or 35NLT® may be known for different medical instruments such a stylet for example, due to their loadability and their corrosion resistance, their suitability for pliable drive shafts however is surprising due to the described special demands, in particularly at a high speed, long operational duration and large curvature, in particular in light of the fact that indeed more than 500 000 000 complete load reversals and in extreme cases more than 1 000 000 000 load reversals can occur with the application as a blood pump.

Alloys with a relatively high iron content or titanium content have been applied until now for the drive shaft, in particular for blood pumps, in order to achieve a high loadability. However, as has been found within the framework of the present invention, one can or indeed one should make do without a high content of iron and titanium as much as possible, in order to permit permanent operation as high rotation speeds. The weight component of iron and titanium is even preferably selected relative low, for example in each case less that 2% by weight or even less than 1% by weight. Basically, one can completely make do without iron and titanium as alloy components, corresponding to weight component of less than 0.1% in each case.

According to a first aspect, the drive shaft can consist completely or at least regionally of an alloy which has a weight component of iron which is less that 2% or preferably less that 1% or particularly preferably less than 0.1%. According to the first aspect, the drive shaft can consist completely or at least regionally of an alloy which has a weight component of titanium which is less that 2% or preferably less than 1% or particularly preferably less than 0.1%.

The drive shaft, the sleeve, the sheath and/or bearing elements which are present as the case may be, consist as much as possible of biocompatible materials, or at least outer surfaces of the respective components consist of a biocompatible material.

According to the second aspect of the invention, the drive shaft can comprise a cavity extending axially within the drive shaft. With regard to the drive shaft, it can therefore be the case of a hollow shaft. The cavity can extend within the drive shaft along a complete longitudinal extension of the drive shaft. A high pliability of the drive shaft with a simultaneously relatively large torsional stiffness can be achieved by such a cavity. The pliability can be increased further if the drive shaft comprises a plurality or a multitude of coaxial windings which run spirally around the cavity of the drive shaft. Torsion and bending stresses can moreover be converted into axial tensile or compressive stresses by way of the windings, by which means the loading of the drive shaft can be reduced. Moreover, it is also possible for the windings of the drive shaft to be arranged in two or more coaxial layers of the drive shaft. The windings within different coaxial layers then preferably have opposite winding directions. Tensile and compressive stresses between the layers and which are caused by torsion stresses can then be completely or partly mutually compensated in this manner. As a whole, bending stresses in the drive shaft can therefore also be reduced.

With regard to the windings of the drive shaft, it is typically the case of windings of a wound wire or several corresponding wound wires. The drive shaft can comprise exactly one or several such wires within each layer, for example 1 to 8 wires, preferably 4 to 6 wires, particularly preferably 5 wires. The wire or the wires preferably consist of the alloy which is described above. The wire or the wires typically in each case have a diameter in a range of about 0.09 mm to about 0.21 mm, preferably of about 0.135 mm to about 0.165 mm. An outer diameter of the drive shaft typically lies in a range of about 0.53 mm to about 1.32 mm, preferably in a range of about 0.79 mm to about 0.97 mm. Outer diameters of the drive shaft below 1 mm are particularly preferred. An inner diameter of the drive shaft typically lies in a range of about 0.17 mm to about 0.39 mm, preferably in a range of 0.25 mm to about 0.31 mm. Axially adjacent windings of the inner layer mutually contact in the case of two concentric layers, whereas axially adjacent windings of the outer layer preferably do not mutually contact (in each case given an alignment of the drive shaft free of curvature), but have an axial distance in a range of about 0.018 mm to about 0.042 mm, preferably of about 0.027 mm to about 0.033 mm.

A small outer diameter of the catheter can also be realised by a small outer diameter of the drive shaft, by which means a reduced traumatisation of the tissue at the location of puncture can be achieved. Further advantages which can be achieved by a low outer diameter of the drive shaft are lower friction and wear problems due to a reduced peripheral speed of the drive shaft, lower vibration problems due to a reduced mass of the drive shaft, as well as reduced disturbance/interference of motor current signals due to vibrations which result from this, and for example a reduced danger of possibly present calcifications within the blood vessel detaching from the vessel wall and possibly getting into the circulation with possibly life-threatening consequences for the patient.

Surprising, it has thus been found that the transmission of adequately high torques, for example for driving an expandable pump rotor in the expanded condition, are also possible with the low outer diameters of the drive shaft of less than 1 mm which are mentioned here, over a longer period. Hereby, in particular the special ranges of the diameter of the wires and which are specified above have been found to be particularly advantageous in the case of a shaft constructed of such wires, wherein it has moreover been found that the optimal region for the diameter of the individual wires is related to the outer diameter of the drive shaft in a non-trivial manner.

Moreover, one can envisage the windings of the drive shaft being manufactured or formed by way of a (high) cold-forming or work-hardening, in order to improve the elasticity and endurance of the drive shaft.

It is possible for the cavity to be filled out with a reinforcement material, completely or within axial sections of the drive shaft, in order to set the stiffness and stability of the drive shaft in the respective axial section and increase it (regionally as the case may be). As already explained in the context of the first aspect of the invention, apart from a sufficient pliability of the drive shaft, an adequate stiffness of the drive shaft is also necessary for a reliable operation of the catheter, in particular at high speeds and longer operational duration, for example in order to permit a stable rotation of the drive shaft, in particular in axial sections of the drive shaft which run distally or proximally outside the sleeve (distal and proximal end-piece of the drive shaft restively). The first and the second aspect of the invention synergistically complement one another in this manner. In a preferred embodiment, one accordingly envisages a distal end-piece of the drive shaft and/or a proximal end or end-piece of the drive shaft being stiffened. The stiffened distal or proximal end or the end-piece preferably has a length between 10 mm to 60 mm, particularly preferably a length between 20 mm and 50 mm. The drive shaft is preferably stiffened in those regions, in which (additionally to the sleeve or instead of it, which is to say in place of the sleeve) bearing elements are arranged for the axial and/or radial mounting of the drive shaft. Moreover, it can also be advantageous to stiffen the drive shaft in the region, in which the drive shaft proximally enters or exits the sleeve and as a result is not guided in the sleeve. Moreover, it can also be advantageous to stiffen the drive shaft in the region, in which the drive shaft enters or exits the sleeve distally. It is indeed in these transition regions that bending loads or other loads, such as oscillation load for example, of the drive shaft, can be reduced by way of a stiffening of the drive shaft.

Materials which are characterised on the one hand by a high stiffness and simultaneously by a relatively high elastic deformability on the other hand are suitable as reinforcement materials for stiffening the drive shaft. In particular, the reinforcement material or the stiffening material should tolerate all bending, to which the catheter or the pump head of the catheter is subjected to during the implantation and during operation. A non-rusting, austenitic steel for example is considered as a reinforcement material, for example a steel according to the material number DIN 1.4310

Alternatively or additionally to the described reinforcement material, a suitable stiffening can also be achieved by way of (axial and/or radial) welding or soldering of (axially or radially) adjacent ones of the windings of the (spiral) drive shaft. Moreover, it is also possible for a certain (and under certain circumstances sufficient) stiffening of the drive shaft to be able to be achieved by way of the distal functional module which is typically fastened on an outer periphery of the drive shaft in a rotationally fixed manner, such as a pump rotor.

According to a third aspect of the invention, the sleeve can be designed as a bearing coil with a plurality of windings. The windings of the bearing coil run around the drive shaft in the axial direction in the manner of a spiral. The bearing coil for example can be a wound flat tape. The flat tape preferably has a width (measured axially) which is larger than the thickness (measured radially) by a factor of at least 3, preferably by factor of 6. Typically, the width of the windings lies in a range of about 0.36 mm to about 0.84 mm, preferably in a range of about 0.54 mm to about 0.66 mm. The thickness of the windings typically lies in a range of about 0.06 to about 0.14 mm, preferably in a range of about 0.09 mm to about 0.11 mm. An inner diameter of the sleeve typically lies in a region between about 0.6 mm and about 1.4 mm, preferably in a range of about 0.9 mm to about 1.1 mm. An outer diameter of the sleeve typically lies in a range of about 0.72 mm to about 1.68 mm, preferably in a range of about 1.08 mm to about 1.32 mm. A pitch of the bearing coil preferably lies in a range of about 0.43 to about 0.98, preferably in a range of about 0.63 to 0.77, wherein the inner diameter of the sleeve corresponds to the outer diameter of the flexible drive shaft, in particular is larger than the outer diameter of the drive shaft.

The bearing coil, in the case that it is designed as a wound flat tape, has low as possible manufacturing tolerances with respect to an (axial) tilting of the windings relative to the longitudinal axis of the bearing coil (in the straight condition without curvature of the bearing coil). The tilting is preferably less than 10°, in particular preferably less than 5°. The inner surface of the sleeve or of the windings of the bearing coils therefore preferably forms cylinder-shaped part-surfaces instead of conical part-surfaces (tilting). A tilting of the windings to the longitudinal axis leads to a reduction of the available bearing surface and to a greater pressure loading of the drive shaft. The lateral edges of the flat tape are preferably rounded as much as possible, in order to avoid pressure peaks upon the drive shaft as much as possible. The radius of curvature of the edges is preferably 0.04 mm or more.

The sleeve can consist completely or at least regionally of an alloy. The description of the alloy of the drive shaft can accordingly also be conferred upon the alloy of the sleeve. In particular, the sleeve can completely or at least regionally consist of the same material, for example of the same alloy as the drive shaft.

In a laboratory test, very good results could be achieved in the fatigue test with the use of the same material for the drive shaft and the sleeve, under a different pulsatile load and with bending radii significantly below 50 mm. This is surprising in many aspects. For example, specifically for reason of patient safety, it is recommended to design the flexible shaft of a wear-resistant material which is relatively hard in comparison to the drive shaft, in order, for example in the case of a shaft breakage which usually leads to a splicing of the shaft in the breakage region, to prevent the drive shaft from rubbing through the sleeve and the even softer sheath of the catheter in subsequent operation, and the rotating openly in the blood vessel. Moreover, in classical engineering, the use of equal materials as sliding partners or friction partners is usually discouraged, since in this case a so-called "eating" or corroding of the work-pieces can occur, which originates from the fact that individual molecules of the two sliding/friction partners connect to one another and can then be torn out of the molecular interconnection of the other part. The fact that it is very difficult or impossible to predict which of the two parts wears is thereby seen as being particularly critical. The use of the same materials for a rapidly rotating flexible shaft and a bearing coil located around this, which is suggested here, is therefore surprising to the man skilled in the art.

The fourth aspect of the invention relates to the design of the proximal coupling element or coupling head of the drive shaft which surprisingly can likewise significantly improve the reliability of the catheter and its suitability for permanent application, in particular if this aspect is combined with one of the other aspects. The basic idea of the fourth aspect lies in being able to often significantly reduce the axial compressive and tensile stresses in the drive shaft if the connection between the coupling element of the drive shaft which itself is as rigid as possible and which is connected to the drive shaft in a rotationally, tractionally and compressively fixed manner, and a coupling element of the drive motor which corresponds to this, although being rotationally fixed, however compensation movements between the coupling element of the drive shaft and the coupling element of the drive motor are possible in the axial direction. For this, the coupling elements of the drive shaft and the drive motor can comprise axial sliding surfaces which correspond to one another and which typically run parallel to the (local) rotation axis or the longitudinal axis of the respective coupling element. The shape of these axial sliding surfaces or their outer or inner contour therefore does not change in the axial direction (thus along the rotation axis or longitudinal axis). The coupling element of the drive shaft for example can have the shape of a square [end] or of another profile piece, which has a cross-sectional area (defined perpendicularly to the rotation axis or longitudinal axis) or outer contour, which is constant in the axial direction, thus along its longitudinal extension or rotation axis. The coupling element of the drive motor can accordingly be designed as a correspondingly designed receiver for the square end or the profile piece.

As already mentioned, the catheter at a distal end of the drive shaft can comprise a pump rotor, for example for delivering blood, which is fixedly connected to the drive shaft. The pump rotor, depending on the configuration, design and the pitch angle of the blading of the pump rotor, can be configured for example for the proximal delivery in the blood (proximal delivery direction, i.e. in the direction of the proximal end of the catheter) or for the distal delivery (distal delivery direction, i.e. in the direction of the distal end of the catheter). The fifth aspect of the invention relates to an axial mounting of the pump rotor, with which a thrust bearing of the catheter is matched to the delivery direction of the pump rotor such that axial bearing forces primarily or exclusively act upon the drive shaft as axial tension (pull) forces (and to a lesser extent or not at all as axial compressive forces). The loading of the drive shaft, particularly at high speeds can be surprisingly significantly reduced by way of this. Moreover, astonishingly, it has been found that the damage to the blood due to the pump operation is lower with such a design of the blood pump. Hereby, in the case of a proximal delivery direction, one envisages arranging the thrust bearing proximally to the pump rotor and being designed to counteract a distally directed axial displacement of the drive shaft (caused by the proximal delivery effect of the pump rotor). The thrust bearing is arranged distally to the pump rotor and is designed to counteract a proximally directed axial displacement of the drive shaft, in the case of a distal delivery direction.

The thrust bearing for example can comprise a first thrust bearing element and a second thrust bearing element, wherein the first thrust bearing element is connected to the drive shaft in a rotationally fixed manner, and the second thrust bearing element is fixedly connected to the sleeve or to the sheath. The first thrust bearing element and the second thrust bearing element comprise sliding surfaces (which can also be indicated as abutment surfaces or end-faces) which face one another, are preferably annular and which block an axial displacement of the drive shaft in at least one direction in the case of a mutual contact. The mentioned sliding surfaces thus overlap one another in the radial direction. The first thrust bearing element can be designed as a radial widening of the drive shaft, but also as a ring which is fastened on the drive shaft, by way of crimping for example. With regard to the second thrust bearing element, it can simultaneously be the case of a radial bearing element, for example with a sliding surface which faces the drive shaft, is preferably designed in a cylindrical manner and is arranged coaxially to the rotation axis of the drive shaft.

Preferably, at least one of the mentioned sliding or abutment surfaces, preferably at least the sliding surface of the first bearing element of the thrust bearing has a profiling such that the two sliding surfaces with an interaction with a (fluid) lubricant form an hydrodynamic plain bearing. The lubricant which is described further below is preferably applied as a lubricant. The profiling has the function of producing bow waves or pressure waves of the lubricant between the two sliding surfaces, wherein these waves run around the drive shaft on rotational operation. This design of the sliding surfaces could surprisingly reduce the arising wear in this region by more than 50%.

The profiling of the respective sliding surface for example can preferably comprise 6 to 24 prominences and/or recesses, which preferably in each case can have a height or depth of about 0.03 mm to about 0.1 mm. Typically, the prominences and/or recesses can be arranged over this sliding surface in a manner distributed uniformly along a peripheral direction or the circumferential direction of the respective sliding surface. The prominences can be the same, just as the recesses can be the same. The prominences can be laterally adjacent the recesses and vice versa. In particular, the profiling can be designed as a sequence of prominences and/or recesses which alternates (along a peripheral direction). The prominences and/or recesses for example can be designed as ribs and grooves respectively, which typically, departing from an inner edge of the sliding surface which faces the drive shaft, extend in the direction of an outer edge of the sliding surface which is away from the drive shaft. Typically, the grooves or ribs run precisely from the inner edge to exactly the outer edge and thus therefore have a length which corresponds to the radially measured width of the respective sliding surface.

The ribs or the grooves typically have a width (measured in the peripheral direction) in a range of about 0.08 mm to about 0.5 mm. The width of the ribs or grooves can be constant, or can change in the radial direction. Typically, the profiling along the peripheral direction of the sliding surface comprises alternating recesses or grooves and prominences or ribs. If the grooves then have a constant width, the ribs then typically widen radially outwards. Such embodiments can often be particularly simply manufactured by way of milling, On the other hand, if the ribs have a constant with, then the grooves typically widen radial outwards. However, it is also possible for the ribs as well as the grooves to widen radially outwards. The last embodiment can be manufactured particularly simply by way of laser cutting. The grooves or ribs can also be designed spirally in regions, thus extend from the inner edge to the outer edge of the sliding surface, on an arcuate path (for example a circular path).

The catheter can comprise the bearing elements mentioned above, as well as further bearing elements for the radial and/or axial mounting of the drive shaft. Zirconium oxide ($ZrO_2$, also called zirconium dioxide, zirconia), in particular zirconium oxide stabilised with yttrium, aluminium oxide ($Al_x$, typically $Al_2O_3$), ceramics as well as alloys described in the context of the first aspect are considered in each case as materials for the bearing elements for example.

According to a sixth aspect of the invention, a cavity or intermediate gap between the drive shaft and the sleeve is filled out with a lubricant which is biocompatible and preferably also physiological. With regard to this lubricant, it can be the case for example of distilled water or an aqueous solution, for example a saline solution and/or a glucose solution. The solution can have a concentration of common salt which is physiological, which is to say is 0.9%. However, an isotonic saline solution or so-called Ringer's solution can also be envisaged. On the one hand, the construction of the catheter can be simplified due to the fact that the lubricant is biocompatible, since an exit of the lubricant into the body does not have to be avoided at all costs. Inasmuch as the materials suggested here are used for the drive shaft, the sleeve and the bearing elements, these components are chemically relatively stable with regard to corrosion by way of these (relatively corrosive) lubricants, so that the application of these lubricants practically does not compromise the reliability and suitability of the catheter for permanent operation. The use of saline solution is particularly advantageous inasmuch as such a solution as a rule is well tolerated by the patient and has no side-effects, in particular even with the presence of a diabetic disease of the patient.

The blood pump arrangement which is suggested here comprises a catheter of the type suggested here, as well as a drive motor for producing a rotational movement or torque. A rotationally fixed and preferably axially displaceable connection exists between the drive motor or the already described coupling element of the drive motor, and the coupling element or coupling head of the drive shaft. With regard to the latter, the description concerning this and in the context of the fourth aspect is referred to. The drive motor can be designed to produce high rotation speeds, for example rotation speeds in a region between 10,000 and 40,000 revolutions per minute. The functional element which is connected to the distal end-piece of the drive shaft in a rotationally fixed manner is designed as a pump rotor. The catheter at its distal end comprises a pump casing, in which the pump rotor is arranged. The pump casing for example can be designed in a manner such that the pump casing (for example whilst being subjected to a (tensile) force acting towards the proximal (or distal) end of the catheter), can be brought from an expanded (or compressed) condition into a compressed (or expanded) condition. The document EP2399639 A1 is referred to concerning the details. With a use of a pump arrangement, one can for example envisage the catheter with its distal end in front being pushed through the femoral artery via the aortic arch into the left ventricle of the heart, and the pump casing remaining in the left ventricle. A downstream tubing which is proximally connected to the pump casing and which then typically runs through the aortic valves, can for example lead the blood which is driven by the pump rotor and which flows out of the pump casing, into the aorta. The proximal end of the catheter and in particular of the drive shaft, as well as the drive motor is arranged outside the body.

With these and similar applications, various external force effects and reverse bending loads act upon the drive shaft and, as the case may be, upon bearing elements of the catheter or of the blood pump arrangement. External force effects and reverse bending loads can be transmitted onto the catheter, for example by an inner wall of the heart, on which the catheter bears or is supported as the case may be (for example via a so-called pigtail tip), by way of pulsatile pressure changes or flow changes of the blood with a ventricle or a blood vessel, for example the left or right ventricle or the aorta, by way of a positional or attitude change of the body, in particular by an abdominal movement or a (leg) movement in the proximity of the puncture location. Despite this loading, blood can be delivered over longer time periods, for example over hours, days or even weeks at high rotation speeds of the pump rotor, for example in the mentioned speed range, such as in the application in of the blood pump arrangement which is described above, with the suggested catheter and the suggested blood pump arrangement.

As is to be deduced for example from "The Sternotomy Hemopump. A second generation intraarterial ventricular assist device" Wampler R K et al., ASAIO J. 1993 July-September; 39(3):M218-23, shaft breakages in the laboratory as a rule can only be realistically simulated under pulsatile compressive loads and bending radii under 2 inches (less than 50.8 mm). The significance of a multiple loading of the shaft is manifested by way of this. Apart from the pump arrangement suggested here, no pumps with a flexible shaft and which have been successfully applied under pulsatile load in the aortic arch over a longer time are known to the applicant. This is due to the processing of the problem of the flexible shaft, which to this date has not been successful. Moreover, until now, in particular in the above-mentioned publication of Wampler the al., the use of a 3-layered shaft instead of a 2-layered shaft was seen as being essential for improving the service life of the flexible shaft. The drive shafts which are suggested here, in contrast have a comparably long or even yet considerably longer durability and loadability at small bending radii (smaller than 50 mm) and a pulsatile loading, than conventional drive shafts, even with a 2-layered design, and thus in embodiments with a significantly smaller diameter than conventional drive shafts.

An outer surface of the drive shaft can surprisingly have a relatively high roughness RZ. The roughness RZ for example can lie in a range of 0.01 µm to 1 µm, preferably in a range of 0.1 µm to 0.8 µm. The roughness RZ for example can be about 0.6 µm. The fact that very good results could be achieved in the endurance test with a relatively high roughness of the surface of the drive shaft is quiet surprising, since due to theoretic considerations, normally an as smooth as possible surface would be preferred, in order to minimise wear due to friction, in particular if a relatively corrosive substance, such as physiological saline solution or glucose solution is used as a lubricant as is suggested here, which with regard to its lubricative effect does not even come close to lubricants common in industry, so that the design principles which are usually applicable to classic engineering evidently cannot be directly conferred even with respect to this.

As already described, a flexible catheter of the type suggested here comprises a drive shaft, a sleeve surrounding the drive shaft and a sheath which surroundings the drive shaft and the sleeve, wherein the drive shaft, the sleeve and the sheath are pliable, wherein the drive shaft at a proximal end of the drive shaft comprises a coupling element for connecting the drive shaft to a drive motor.

The drive shaft moreover can comprise an outer diameter of less than 1 mm. The drive shaft and/or the sleeve, at least regionally preferably consists of a material which has a tensile strength between 1800 N/mm$^2$ and 2400 N/mm$^2$, preferably between 2034 N/mm$^2$ and 2241 N/mm$^2$. The drive shaft and/or the sleeve at least regionally can consist of a non-metallic or a metallic material. In the case of a metallic material, it is hereby preferably the case of an alloy as already described further above, which thus contains in each case at least 10% by weight of chromium, nickel and cobalt. This alloy can have the features already described above. The drive shaft and the sleeve can completely or at least regionally consist of the same material. Moreover, as has already been described further above, a surface of the drive shaft can have a roughness of between 0.01 µm and 1 µm, preferably between 0.1 µm and 0.8 µm. Of course, the catheter can have all of the features and feature combinations, which have been described beforehand and are described hereinafter.

Figure 2:
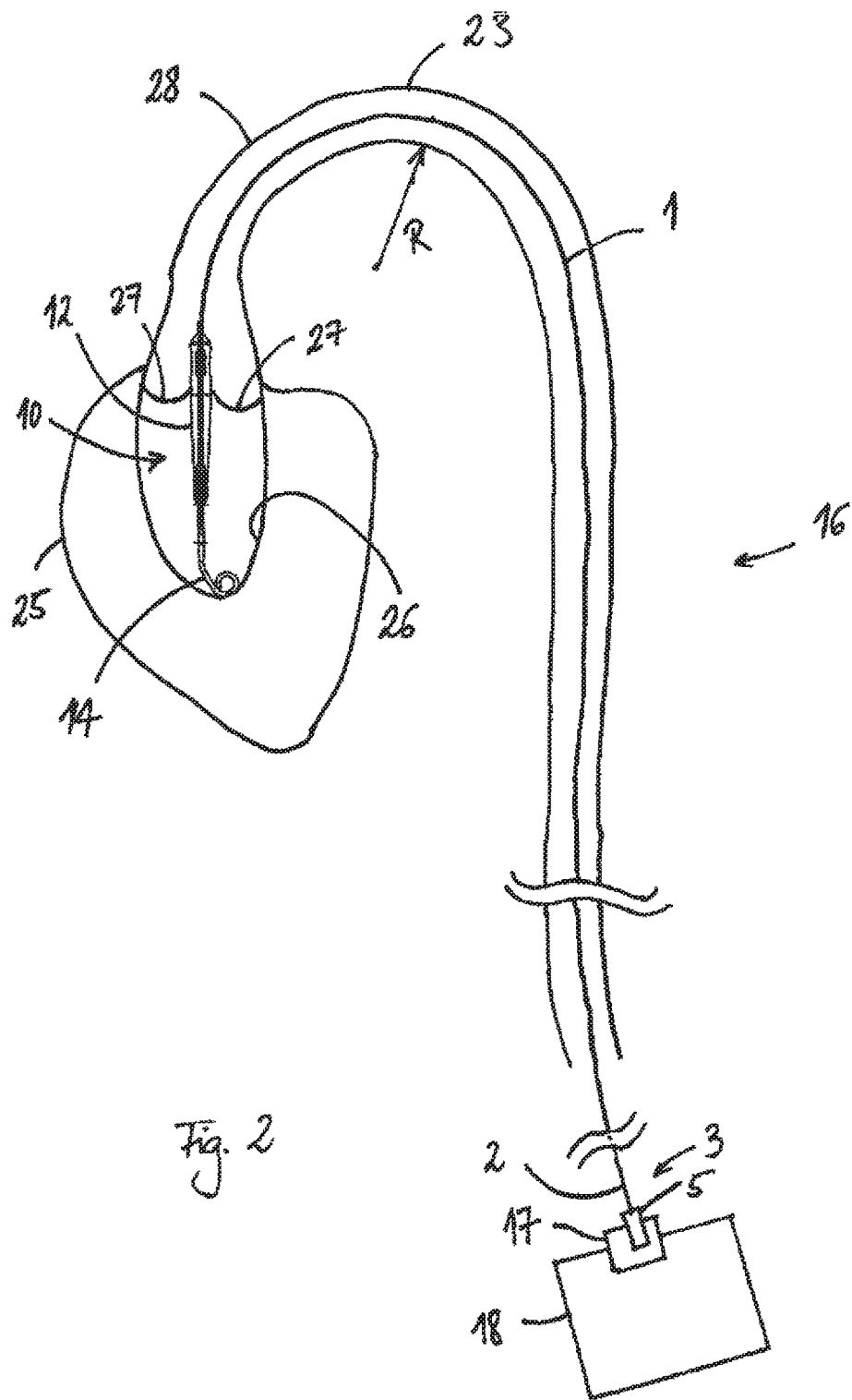
Figure 3:
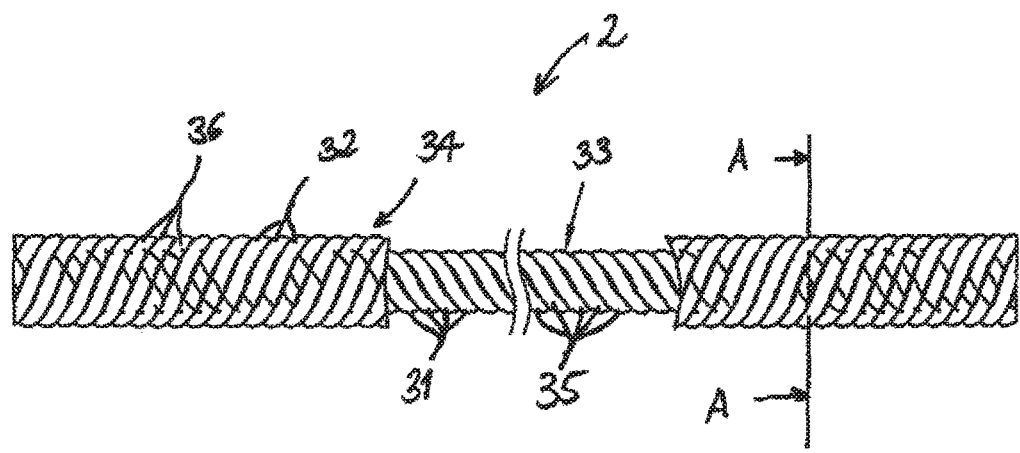
Figure 4:
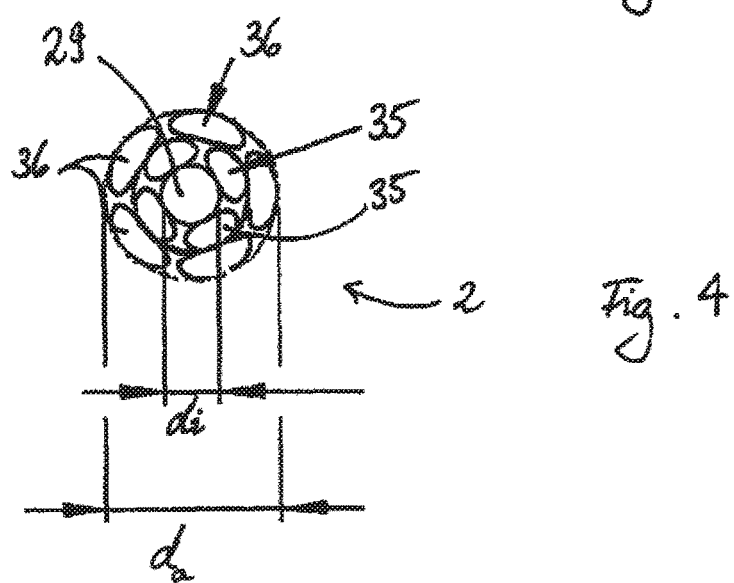
Figure 5:
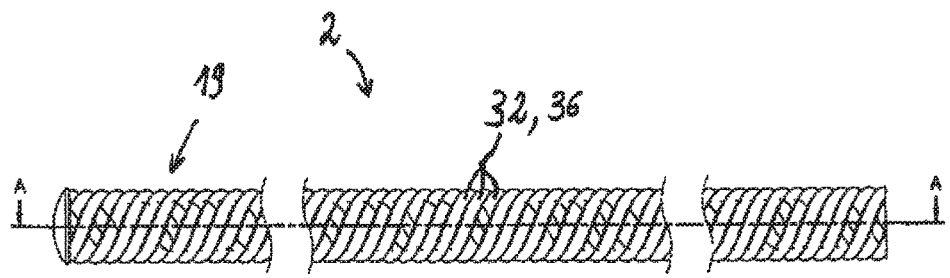
Figure 6:
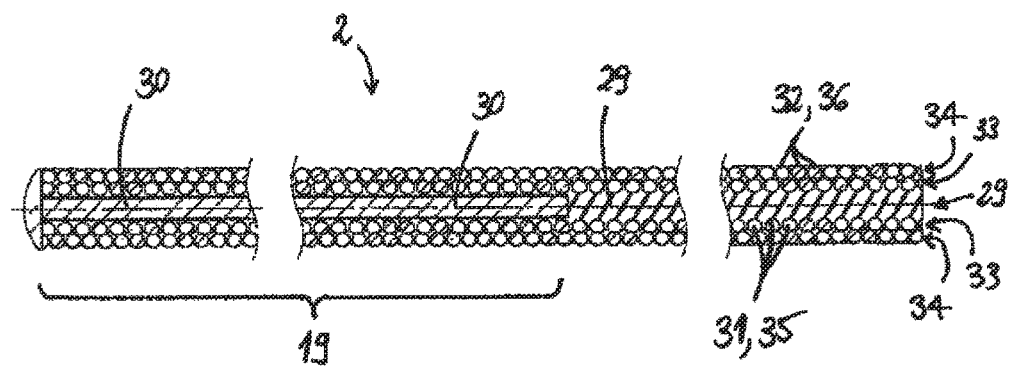
Figure 7:
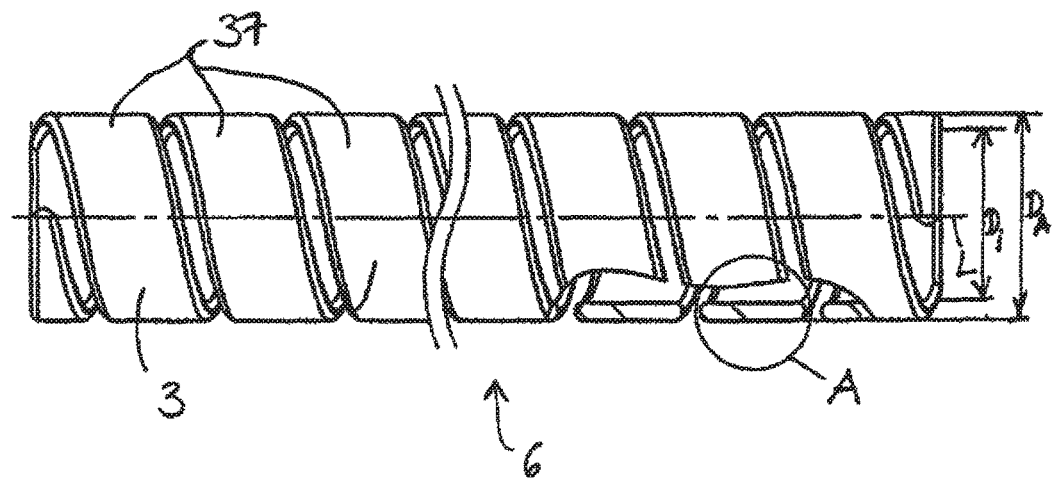
Figure 8:
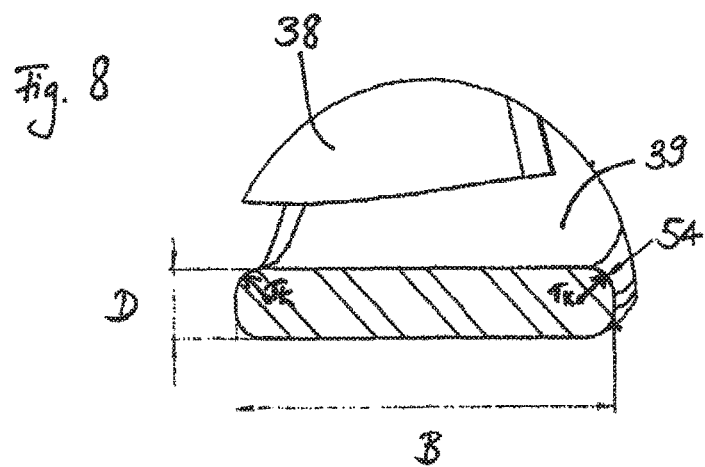
Figure 9:
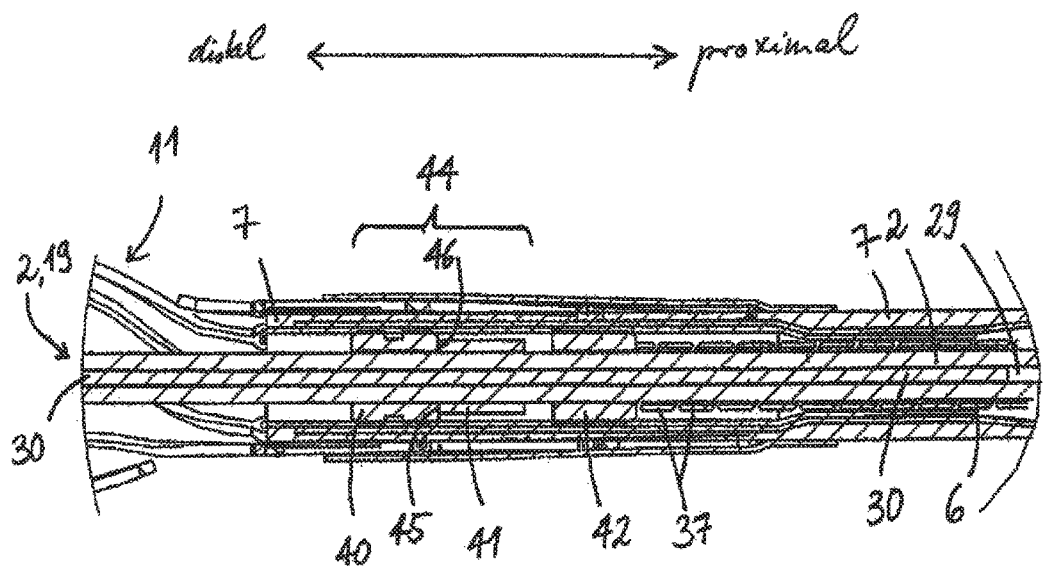
Figure 10:
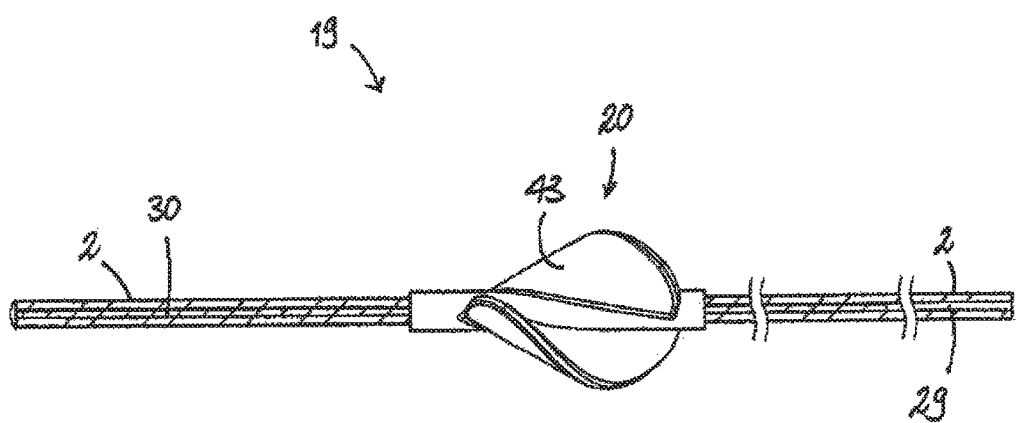
Figure 11:
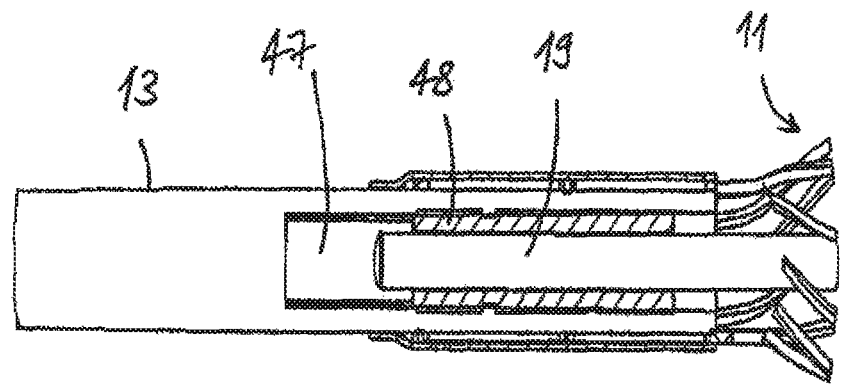
Figure 12:
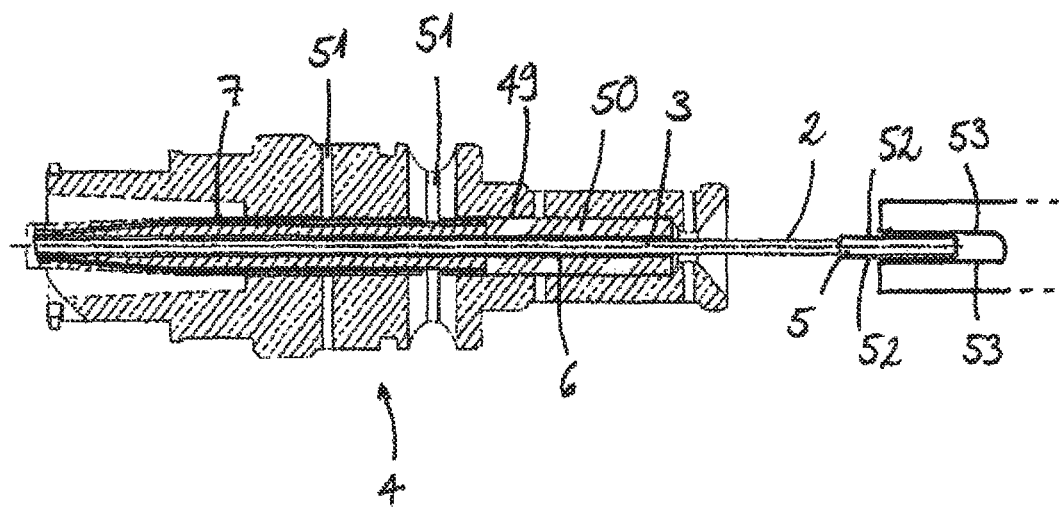
Figure 13:
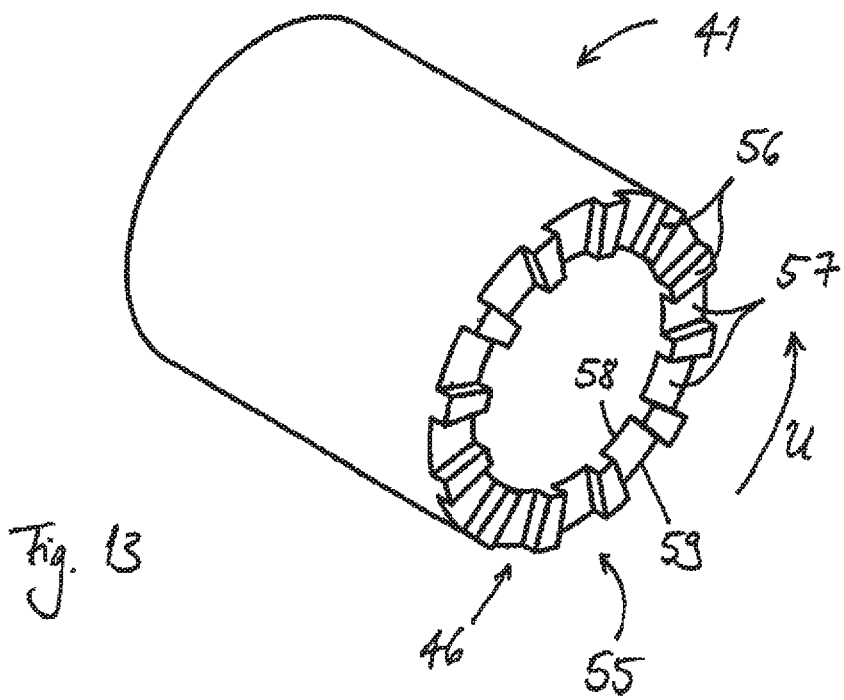
Figure 14:
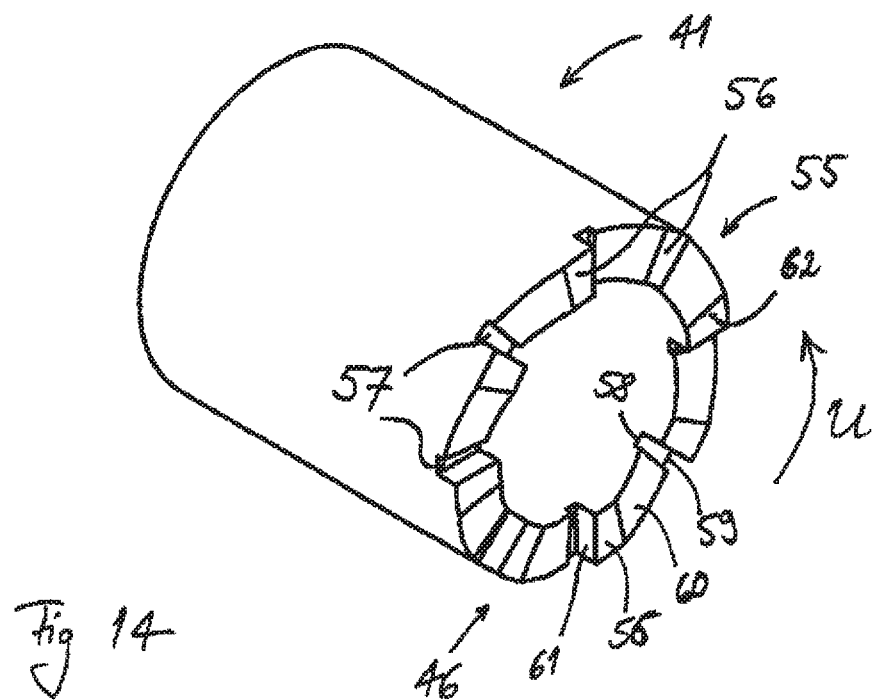

The mentioned aspects of the present invention are hereinafter explained in more detail by way of a special embodiment example of a catheter of the type suggested here and of a blood pump arrangement of the type suggested here, which are represented schematically in FIGS. 1 to 16. There are shown in:

FIG. 1 a catheter of the type suggested here, in a lateral view,

FIG. 2 a blood pump arrangement with the catheter shown in FIG. 1, in an implanted condition, FIG. 3 axial sections of parts of the drive shaft of the catheter of FIG. 1, in a lateral view, FIG. 4 a cross section through the drive shaft which is represented in FIG. 3, at the location which is characterised there at AA, FIG. 5 a distal end-piece of the drive shaft which is stiffened with a reinforcement material, in a lateral view, FIG. 6 a longitudinal section through the end-piece which is shown in FIG. 5, at the location which is characterised there at AA, FIG. 7 a sleeve of the catheter which is shown in FIG. 1, in a lateral view, FIG. 8 a cross section through a part-region of the sleeve shown in FIG. 7, said part region being characterised there at A, FIG. 9 a longitudinal section through the catheter which is shown in FIG. 1, in the axial part-section which is characterised there at Y, FIG. 10 the distal end-piece which is represented in FIGS. 5 and 6, with a pump rotor which is fastened on this in a rotationally fixed manner, FIG. 11 a longitudinal section through the catheter which is show in FIG. 1, in the axial part-section which is characterised there at Z, FIG. 12 a longitudinal section through a coupling module of the catheter which is shown in FIG. 1, and FIG. 13 an embodiment example of a bearing element of an thrust bearing shown in FIG. 9, in a perspective representation, FIG. 14 a further embodiment example of the bearing element which is shown in FIG. 13, likewise in a perspective representation, FIG. 15 readings of yield point, tensile strength and elongation at break, for different values of the work-hardening degree for the material 35NLT®, and FIG. 16 diagrammatic representation of the readings of tensile strength and elongation at break, which are specified in FIG. 15, as functions of the work-hardening degree for the material 35NLT®.

Recurring features or features which correspond to one another are characterised by the same reference numerals in the figures.

A special embodiment of a flexible catheter 1 of the type suggested here is represented schematically in FIG. 1. The catheter 1 comprises a pliable drive shaft 2, of which in this figure a proximal end-piece 3 is to be seen, said end-piece projecting out of a proximal coupling module 4 (cantilever), and at its proximal end the drive shaft 2 comprises a coupling element 5 for the connection of the drive shaft 2 to a drive motor, cf. FIG. 2. The catheter 1 moreover comprises a pliable sleeve 6 (not shown here, but see FIGS. 7 to 9) which surrounds the drive shaft 2 and radially mounts it, and a pliable sheath 7 surrounding the drive shaft 1 and the sleeve 6. Thus whereas the coupling module 4 and the proximal end-piece 3 of the drive shaft 2 are arranged at a proximal end 8 of the catheter 1, the catheter 1 at a distal end 9 of the catheter 1 comprises a pump head 10 with a pump casing 11, with a terminating housing 13 which is arranged distally to the pump casing 11 and is for drive shaft 2, and a downstream tubing 12 which is proximally adjacent the pump casing 11 (elements running within the downstream tubing 12 are represented dashed in FIG. 1). A support element 14 in the form of a so-called pigtail tip is arranged distally on the terminating housing 13. The catheter 1 moreover comprises a lock 15. The function of the lock is to radially compress the pump head 10 when this is pulled into the lock 15. The pump head 10 in this compressed condition for example can be subsequently led through an introduction lock (not represented in the figures) and be implanted through this. The introduction lock for example can be fixed at a puncture location on or in the body of a patient, in order in this manner to likewise support the catheter 1 at this location. The document EP2399639 A1 is referred to in this context.

This catheter as part of a blood pump arrangement 16 is represented in an implanted condition in a greatly schematic manner in FIG. 2. What is shown is the use or application of the catheter 1 and the blood pump arrangement 16, with which the drive shaft 2 of the catheter 1 is connected via the coupling element 5 to a corresponding coupling element 17 of a drive motor 18 of the blood pump arrangement 1, in a rotationally fixed manner (but axially displaceable manner, see description concerning FIG. 12). The drive motor 18 is designed to produce high rotation speeds in a region between 10,000 and 40,000 revolutions per minute.

As is shown in FIG. 10, a functional element which is designed as a pump rotor 20 is connected in a rotationally fixed manner to a distal end-piece 19 of the drive shaft 2.

The pump rotor 20 is arranged within the pump casing 11 which in this embodiment example is designed such that it can be brought from a radially expanded condition into a radially compressed condition. This for example can be effected with the help of a lock 15 or the introduction lock mentioned above, preferably by way of the pump casing 11, whilst being subjected to a (tensile) force acting towards the proximal end 8 of the catheter, being at least partly pulled into the respective lock and thereby being compressed along a radial direction running transversely to the longitudinal direction. The pump casing 11 can accordingly be brought from the compressed into the expanded condition by way of a reverse force. The document 2399639 A1 is also referred to here.

With the application of the pump arrangement 2 which is represented in FIG. 2, the catheter 1 with its distal end 9 in front, is inserted through a puncture location 21 into the body of a patient in its femoral artery 22 and is pushed along this via the aortic arch 23 into the left ventricle 24 of the heart 25. The pump casing 11 is thus positioned in the left ventricle 24 such that it is supported by the support element 14 on an inner wall 26 of the left ventricle 24, and the downstream tubing 12 runs through the aortic valves 27 into the aorta 28. The blood which is driven by the pump rotor 20 and which flows out of the pump casing is thus led through the downstream tubing 12 into the aorta 28. The proximal end 8 of the catheter 1, the proximal end-piece 3 of the drive shaft 2 as well as the drive motor 18 are arranged outside the body.

In this embodiment example, an (axial) total length of the catheter and an (axial) total length of the drive shaft 2 are in each case about 150 cm (corresponding to an implantable length of about 140 cm), an (axial) total length of the distal end 9 of the catheter (including pump head 12 and support element 14) is about 13.5 cm, in order to permit this application. The flexibility or the pliability of the catheter 1, thus in particular of the drive shaft 6, the sleeve 6 and the sheath 7 are so large that the catheter 1 can be implanted and operated, as has been described above. For this, these components must be able to be elastically curved by 180° at least within the distal end 9 of the catheter, with the typically radius of curvature R of the aortic arch 23 of about 30 mm, as is shown in FIG. 2, without plastic deformation, in particular of the drive shaft 2 thereby occurring.

As is shown in FIGS. 4 and 6, the drive shaft 2 is designed as a hollow shaft and comprises a cavity 29 extending axially within the drive shaft 2, in order to achieve a high pliability of this drive shaft 2. The cavity 29 extends along the total length of the drive shaft 2. This cavity 29 however is completely filled out with a reinforcement material 30, a co-called core, at least within the roughly 4.5 cm long distal end-piece 19 of the drive shaft, see FIGS. 6, 9 and 10 and the associated description further below, in order here to achieve an adequate stiffness and oscillation stability of the drive shaft 2 or of the distal end-piece 19 of the drive shaft.

The drive shaft 2 comprises a multitude of coaxial windings 31, 32 which run spirally around the cavity 29 of the drive shaft 2, in order to convert torsion and bending stresses into axial tensile and compressive stresses. The windings 31, 32 are arranged in two coaxial layers 33, 34 which is to say plies, of the drive shaft 2, wherein the windings 31 are arranged co-radially (with the same winding radius) within the inner layer 33, and the windings 32 are arranged co-radially within the outer layer. The windings 31 of the inner layer 33 have an opposite winding direction compared to the windings of the outer layer 34, so that tensile and compressive stresses can be compensated between the layers. In the shown example, the drive shaft in the inner layer 33 comprises four wires 35 which are wound coaxially and co-radially around the cavity 29, and in the outer layer 34 five wires which are wound coaxially and co-radially around the cavity, wherein axially adjacent windings 31 of the inner layer mutually contact, but axially adjacent windings (winding packet of five wires in each case) 32 of the outer layer however do not mutually contact (in each case given an alignment of the drive shaft which is free of curvature), but have an axial distance of about 0.03 mm. An outer diameter $d_a$ of the drive shaft in the present example is about 0.88 mm and an inner diameter $d_i$ about 0.28 mm. The wires have a circularly round cross section with a diameter of about 0.15 mm. In the present example, the peripheral direction of the windings 36 of the outer layer 34 is counter to the designated rotation direction of the drive shaft 2 for the (proximal) delivery of blood.

Here, this rotation direction corresponds to the clockwise direction (defined for a viewing direction from the proximal to the distal end of the drive shaft). The torque to be transmitted in this case leads to the outer layer tending to contract and shorten. Since the inner layer 33 has an opposite tendency due to its opposite winding direction, these tendencies advantageous largely cancel each out. Basically, this mutual compensation can also be achieved in the reverse case, when specifically the winding direction of the outer layer corresponds to the rotation direction and the winding direction of the inner layer is opposite to the rotation direction of the drive shaft.

The wires 35, 36 of the drive shaft 2 consist completely of an alloy, which as alloy components contain about 35% by weight of nickel, about 35% by weight of cobalt, about 20% by weight of chromium and about 10% by weight of molybdenum. These alloy components of the alloy can in each case also be greater or smaller by up to 3% by weight, or greater or smaller in each case by up to 2% by weight. With regard to the alloy, in this example it is particularly the case of 35NLT®, but it could just as easily be the case of MP35N®. The weight component of iron in the wires is thus less that 1% by weight and the weight component of titanium is less than 0.1% by weight. The alloy and the windings 31, 32 of the drive shaft are manufactured or formed amid the application of high cold-forming and work-hardening. In this example, a non-rusting, austenitic steel according to the material number DIN 1.4310 (X10CrNi18-8) is selected as a reinforcement material 30 for stiffening the drive shaft 2. Alternatively, any other material which fulfils the demands specified further above in this context could also be selected as a reinforcing material.

The sleeve 6 is represented in FIGS. 7 and 8, which in the shown example is designed as a bearing coil with a multitude of windings 37, wherein the windings 37 of the bearing coil run around the drive shaft 2 in the axial direction in the manner of a spiral. In the present example, the bearing coil is given by a wound-on flat tape 38. The flat tape 38 has a width B (measured axially) which is larger than the thickness D (measured radially) by a factor of about 6. In the present example, the width B of the windings 37 is 0.6 mm and the thickness D of the windings 37 is 0.1 mm. The windings 37 are moreover angled which is to say tilted as little as possible relative to the longitudinal axis L of the bearing coil (in the straight condition without a curvature of the bearing coil), where possible by less than 5°, so that an inner surface 39 of the sleeve 6 which is formed by the windings 37 is as cylindrical as possible or forms as cylindrical as possible part-surfaces. Moreover, the lateral edges 54 of the flat tape are preferably as rounded as possible, with a radius of curvature $r_k$ of about 0.04 mm. The radius of curvature $r_k$ of the edges 54 is preferably more than 0.04 mm. Moreover, an inner diameter $D_I$ of the sleeve 6 is about 1 mm and an outer diameter $D_A$ of the sleeve about 1.2 mm and has a gradient/pitch of about 0.7. The sleeve 6 or the flat tape 38 in this example consists of the same alloy as the wires 35, 36 of the drive shaft 2, thus here of 35NLT®, but could however also be manufactured of another one of the materials which are mentioned for this.

The drive shaft 2 and the sleeve 6 could also consist of materials other than the alloys mentioned here. The drive shaft 2 is preferably manufactured from the same material as the sleeve 6. Moreover, a surface of the drive shaft 2 can have a roughness RZ of about 0.6, by which means surprisingly a particularly good wear resistance is achieved. Surprisingly good wear characteristics and thus a high operational reliability can be achieved by way of these measures which are quite simple to implement.

A longitudinal section through the axial section of the catheter 1 which is indicated at Y in FIG. 1 is represented schematically in FIG. 9. In this section, the catheter 1 comprises bearing elements 40, 41, 42 which are arranged proximally to the pump rotor 20, for the radial and axial mounting of the drive shaft 2.

The arrangement and design of these bearing elements 40, 41, 42 is matched to the pump rotor 20 of the catheter 1 which is shown in FIG. 10. This pump rotor 20 has a blading 43, whose configuration, design and pitch angle are configured for delivering the blood proximally (proximal delivery direction, i.e. in the direction of the proximal end of the catheter). The bearing elements 40 and 41 form a thrust bearing 44 which is arranged proximally to the pump rotor 20 (The bearing element 41 is a first thrust bearing element of the thrust bearing 44, and the bearing element 40 is a second thrust bearing element of the thrust bearing 44). The thrust bearing 44 on account of the design and arrangement of these (thrust) bearing elements 40, 41, is designed to counteract a distally directed axial displacement of the drive shaft 2 (caused by the proximal delivering effect of the pump rotor 20). Axial bearing forces acting mainly act upon the drive shaft 2 as tension forces on operation of the blood pump arrangement in this manner.

The (first) bearing element 41 is preferably designed in an annular manner and is connected to the drive shaft 22 in a rotationally fixed manner, for example by way of crimping. The (second) bearing element 40, just as the bearing element 42, in contrast is fixedly connected to the sleeve 6 and to the sheath 7. The bearing elements 40, 41 have annular sliding surfaces 45 and 46 respectively which face one another and which block an axial displacement of the drive shaft 2 in the distal direction in the case of a mutual contacting, The sliding surface 46 of the (first) bearing element 41 has a profiling, see FIGS. 13 and 14 and the associated description below, by which means the formation of a stable lubricant film between the two sliding surfaces 45, 46 is encouraged, and basically a design of the thrust bearing 44 as a hydrodynamic sliding bearing is rendered possible. The lubricant film which is to say the hydrodynamic bearing in this example is formed with the lubricant which is described further below. The bearing element 40, as also the bearing element 42, is moreover designed as a radial bearing element in each case with a sliding surface which faces the drive shaft 2, is designed in a cylindrical manner and is arranged coaxially to the rotation axis of the drive shaft 2.

Moreover, as is to be recognised in FIG. 9, the drive shaft 2 is reinforced by the reinforcement material 30, in the axial sections, in which it distally exits from the sleeve 6 which is to say is mounted by the bearing elements 40, 41, 42.

A longitudinal section through the axial section of the catheter 1 which is characterised by the reference numeral Z in FIG. 1 is schematically represented in FIG. 11, and this in particular includes the terminating housing 13 which is adjacent the pump casing 11. The terminating housing 13 is designed in a tubular manner and comprises a distal bearing channel 47 and a bearing element 47 which is arranged therein, for the radial mounting of the distal end-piece 19 of the drive shaft 2. The cavity 47 in particular is dimensioned sufficiently large, in order to permit axial compensation movements of the drive shaft 2.

A longitudinal section through the proximal coupling module 4 shown in FIG. 1 is represented schematically in FIG. 12, said coupling module comprising a proximal bearing channel 49 for the proximal end-piece 3 of the drive shaft 2, wherein the proximal end-piece 3 of the drive shaft 2 runs axially through the bearing channel 49 and projects axially out of the proximal coupling module 4. A bearing element 50 for the radial stabilisation or mounting of the proximal end-piece 3 of the drive shaft 2 is arranged in the bearing channel 49. The sleeve 6 extends axially through this bearing element 50 up to its proximal end. The bearing element 50 in this embodiment has the function of radially stabilising and supporting the sleeve 6 from the outside. In an alternative embodiment, the sleeve 60 does not run through the bearing element 50, but ends (coming from the distal side) at the distal end of the bearing element 50. In this case, the bearing element 50 for example is designed as a sliding bearing or as a roller bearing. The proximal end-piece 3 can be stiffened by the reinforcement material 30, just as the distal end-piece 19, in particular in the axial sections, in which the drive shaft exits out of the bearing channel 49 or is mounted by the bearing element 50. The bearing elements 40, 41, 42, 48 and 50 preferably consist of zirconium oxide, preferably in the form stabilised with yttrium, of aluminium oxide, of a ceramic or of the same materials as the wires 35, 36 of the drive shaft 2.

The coupling housing 4 moreover comprises channels 51 for the feed and discharge of the lubricant, wherein the channels are connected in a fluid-leading manner to the bearing channel 49 as well as to an intermediate space between the sleeve 6 and the drive shaft 2. According to the sixth aspect of the invention, an intermediate space or intermediate gap between the drive shaft and the sleeve is filled with a lubricant which is biocompatible and preferably also physiological. The lubricant is biocompatible and in this example is the case of distilled water, but it could also be a physiological saline solution or glucose solution.

The coupling element 5 of the drive shaft 2 is designed as rigidly as possible and is connected to the proximal end-piece 3 of the drive shaft 2 in a manner fixed with regard to rotation, traction and compression. The coupling element 5 of the drive shaft as well as the coupling element 17 of the drive motor 18, which in this example is designed as a receiver for the coupling element 5, comprises axial sliding surfaces 52 and 53 respectively, which correspond to one another, for forming a rotationally fixed, but axially displaceable connection. These sliding surfaces run parallel to the longitudinal axis of the respective coupling element 5 and 17 respectively and do not change their shape along the longitudinal axis of the respective coupling element 5 and 17 respectively. With this example, with regard to the coupling element 5 of the drive shaft 2 it is the case of a square end.

The sheath 7 can consist completely or at least regionally of a plastic, for example of polyurethane, in particular of a carbothane or a urethane. The sheath preferably has a metal reinforcement, which for example can consist of the alloy which is suggested for the drive shaft, thus for example of MP35N®

FIGS. 13 and 14 in each case show a schematic perspective representation of an embodiment example of the first bearing element 41 of the thrust bearing 44 which is shown in FIG. 9. The sliding surface 46 of the respective bearing element 41 comprises a profiling 55, so that the two sliding surfaces 45, 46 with an interaction with the lubricant form a hydrodynamic sliding bearing, by which means a wear volume of the sliding surfaces 45, 46 or of the two bearing elements 40, 41 can be significantly reduced. In the embodiments represented here, the profiling 55 of the respective sliding surface 46 comprises several prominences 56 and recesses 57. In the example represented in FIG. 13, there are exactly 12 prominences and 12 recesses, in the example shown in FIG. 14 there are precisely 8 prominences and 8 recesses, wherein the prominences 56 and recesses 57 in each case are arranged uniformly distributed over the sliding surface 46 along a peripheral direction or circumferential direction (indicated in each case by a arrow characterised by U in the figures) of the respective sliding surface 46 and are designed as an alternating sequence of ribs and grooves.

These ribs and grooves extend in each case from an inner edge 58 of the respective sliding surface 46 which faces the drive shaft 2, up to an outer edge 59 of the respective sliding surface 46 which is away from the drive shaft 2. In the example represented in FIG. 13, the ribs in each case have a height (this corresponds to the depth of the respective laterally adjacent groove) of about 0.06 mm and an average width (measured in the peripheral direction U) of about 0.2 mm. In the example represented FIG. 13, the prominences 55 which are designed as ribs in each case have a maximal height of about 0.1 mm, wherein each prominence has a leading surface 60 and a trailing surface 61, wherein the leading surface 60 advances with respect to the trailing surface 61 given a rotation of the bearing element 41 in the designated rotation direction along the peripheral direction U (in the clockwise direction given a viewing direction to the distal end 9 of the catheter 1).

This leading surface 60 is inclined or bevelled with respect to the longitudinal axis of the bearing element 41, in a manner such that the prominence 56 reduces or tapers upwards (i.e. in the direction of the opposite sliding surface 45 of the second bearing element 40, thus in the distal direction in the present example). Basically, thus in any other embodiment examples of profilings of the bearing element 41, a more uniform bow wave formation of the lubricant can be achieved, and by way of this a more stable lubricant film can be formed, with such inclined which is to say bevelled leading surfaces 60. On its respective upper side 62, each of the prominences 56 has an average width (measured in the peripheral direction U) of about 0.3 mm, wherein the width of the prominence 56 increases in the radial direction. An average width (measured in the peripheral direction U) of the grooves 57 in this example is about 0.1 mm, wherein the width of the grooves also increases radially outwards. The embodiments which are shown in FIGS. 13 and 14 can be manufactured for example by way of a (cutting) laser.

The dependency between the material characteristics yield point, tensile strength, elongation at break and cold work-hardening degree, based on the details of the manufacturer Fort Wayne Metals, is represented with the example of the material 35NLT in FIGS. 15 and 16. By way of this example, it is shown that different heat-treatment conditions and work-hardening degrees of a material can generally lead to very different material characteristics.

For example, if the drive shaft 2 and/or the sleeve 6 of the embodiment example shown in FIGS. 1 to 15 consist of 35NLT, then the work-hardening degree of this material is preferably at about 35 to 70%, particularly preferably at 50% to 60%, so that here a tensile strength of about 2000 to 2200 Mpa, for example 2068 MPa is achieved, and a elongation at break of 3.5% is not fallen short of. In the foregoing disclosure, it will be understood that the term "about" should be taken to mean±20% of the stated value, as is known in the art.

LIST OF REFERENCE NUMERALS 1 catheter
2 drive shaft
3 proximal end-piece of the drive shaft
4 coupling module
5 coupling element of the drive shaft
6 sleeve
7 sheath
8 proximal end of the catheter
9 distal end of the catheter
10 pump head
11 pump casing
12 downstream tubing
13 terminating housing
14 support element
15 lock
16 blood pump arrangement
17 coupling element of the drive motor
18 drive motor
19 distal end-piece of the drive shaft
20 pump rotor
21 puncture location
22 femoral artery
23 aortic arch
24 left ventricle
25 heart
26 inner wall
27 aortic valve
28 aorta
29 cavity
30 reinforcement material
31 winding of the drive shaft
32 winding of the drive shaft
33 coaxial layer of the drive shaft
34 coaxial layer of the drive shaft
35 wire of the drive shaft
36 wire of the drive shaft
37 winding of the sleeve
38 flat tape
39 inner surface of the sleeve
40 bearing element
41 bearing element
42 bearing element
43 blading
44 thrust bearing
45 sliding surface
46 sliding surface
47 bearing channel of the terminating housing
48 bearing element
49 bearing channel of the coupling module
50 bearing element
51 channel for the lubricant
52 sliding surface
53 sliding surface
54 edge
55 profiling
56 prominence
57 recess
58 inner edge
59 outer edge
60 leading surface
61 trailing surface

The invention claimed is:

1. A flexible catheter comprising:
a drive shaft;
a sleeve surrounding the drive shaft; and
a sheath surrounding the drive shaft and the sleeve, wherein the drive shaft, the sleeve and the sheath are configured to be pliable, wherein the drive shaft at a proximal end of the drive shaft comprises a coupling element for connecting the drive shaft to a drive motor; and
wherein the drive shaft has an outer diameter of less than 1 mm, and at least in regions consists of a material configured to have a tensile strength between 1800 N/mm$^2$ and 2400 N/mm$^2$.

2. A catheter according to claim 1, wherein the material of the drive shaft has a tensile strength between 2034 N/mm$^2$ and 2241 N/mm$^2$.

3. A catheter according to claim 2, wherein the drive shaft at least regionally consists of a metallic material.

4. A catheter according claim 3, wherein the metallic material is an alloy which contains at least 10% by weight of chromium, nickel and cobalt.

5. A catheter according to claim 4, wherein the catheter comprises at least one bearing element for a radial and/or axial mounting of the drive shaft within the catheter, wherein at least one of the at least one bearing element comprises zirconium oxide, in particular yttrium-stabilised zirconium oxide, aluminium oxide, a ceramic and/or the alloy.

6. A catheter according to claim 4, wherein the sleeve at least regionally consists of the same material as the drive shaft and/or the alloy.

7. A catheter according to claim 4, wherein the alloy contains 30%-40% by weight of nickel, 30%-40% by weight of cobalt and/or 15%-25% by weight of chromium.

8. A catheter according to claim 4, wherein the alloy contains 35% by weight of nickel, 35% by weight of cobalt, 20% by weight of chromium and 10% by weight of molybdenum, or differs from this in each case by up to 3% by weight.

9. A catheter according to claim 1, wherein a surface of the drive shaft has a roughness RZ between 0.01 µm and 1 µm.

10. A catheter according to claim 1, wherein a surface of the drive shaft has a roughness RZ between 0.1 µm and 0.8 µm.

11. A catheter according to claim 1, wherein the outer diameter of the drive shaft lies in a range of about 0.53 mm to about 1 mm.

12. A catheter according to claim 1, wherein the outer diameter of the drive shaft lies in a range of about 0.79 mm to about 0.97 mm.

13. A catheter according to claim 1, wherein the drive shaft comprises a cavity extending axially within the drive shaft.

14. A catheter according to claim 13, wherein the drive shaft comprises a plurality of coaxial windings which run spirally round the cavity of the drive shaft.

15. A catheter according to claim 14, wherein the windings are arranged in two or more coaxial layers of the drive shaft, wherein the windings within different coaxial layers have opposite winding directions.

16. A catheter according to claim 14, wherein the windings are formed by at least one wound wire of the drive shaft, wherein the at least one wire has a diameter in a range of about 0.09 mm to about 0.21 mm.

17. A catheter according to claim 16, wherein the diameter of the at least one wire lies in a range of about 0.135 mm to about 0.165 mm.

18. A catheter according to claim 13, wherein at least one axial section of the cavity of the drive shaft is filled out with a reinforcing material, for stiffening the drive shaft in the at least one axial section.

19. A catheter according to claim 14, wherein at least one region of the catheter is stiffened by welding or soldering of selected axially or radially adjacent ones of said windings.

20. A catheter according to claim 14, wherein at least one region of the catheter is stiffened by fastening a module to an outer periphery of the drive shaft in a rotationally fixed manner.

21. A catheter according to claim 1, wherein a distal part of the drive shaft is flexible.

22. A catheter according to claim 1, wherein a distal end-piece of the drive shaft is stiffened.

23. A catheter according to claim 22, wherein the stiffened distal end-piece has a length between 10 mm to 60 mm.

24. A catheter according to claim 1, wherein the catheter at a distal end of the drive shaft comprises a pump rotor which is fixedly connected to the drive shaft.

25. A catheter according to claim 24, wherein the pump rotor is designed for producing a proximally directed flow, wherein the catheter comprises a thrust bearing which is arranged proximally to the pump rotor and which is designed to counteract a distally directed axial displacement of the drive shaft, or that the pump rotor is designed for producing a distally directed axial flow, wherein the catheter comprises a thrust bearing which is arranged distally to the pump rotor and which is designed to counteract a proximally directed axial displacement of the drive shaft.

26. A catheter according to claim 25, wherein the thrust bearing comprises at least one first bearing element and second bearing element, wherein the first bearing element is connected to the drive shaft in a rotational fixed manner and the second bearing element is connected to the sleeve or to the sheath in a fixed manner, wherein the first bearing element and the second bearing element comprise sliding surfaces which face one another and which block an axial displacement of the drive shaft in at least one direction given a mutual contacting.

27. A catheter according to claim 26, wherein the sliding surface at least of the first bearing element comprises a profiling for forming a hydrodynamic sliding bearing.

28. A catheter according to claim 27, wherein the profiling of the sliding surface comprises several prominences or recesses.

29. A catheter according to claim 28, wherein the prominences or recesses in each case have a height and depth respectively of about 0.03 to about 0.1 mm.

30. A catheter according to claim 28, wherein the prominences or the recesses are designed as ribs or grooves, which departing from an inner edge of the sliding surface which faces the drive shaft extend in the direction of an outer edge of the sliding surface which is away from the drive shaft.

31. A catheter according to claim 30, wherein the ribs or the grooves have a width in a range of about 0.08 mm to about 0.5 mm.

32. A catheter according to claim 1, wherein the sleeve is designed as a bearing coil with a multitude of windings, wherein the windings run spirally around the drive shaft in the axial direction.

33. A catheter according to claim 32, wherein the bearing coil is a wound flat tape.

34. A catheter according to claim 1, wherein an intermediate space between the drive shaft and the sleeve is filled with a biocompatible lubricant.

35. A catheter according to claim 34, wherein the lubricant is distilled water, a saline solution, or a glucose solution.

36. A catheter according to claim 1, wherein the proximal coupling element of the drive shaft comprises axial sliding surfaces which are uniformly designed along a longitudinal axis of the coupling element, for a rotationally fixed and axially displaceable connection to the drive motor.

37. A catheter according to claim 1, wherein total lengths of the drive shaft, of the sleeve and of the sheath in each case lie in a range between 50 cm and 200 cm.

38. A blood pump arrangement comprising a catheter according to claim 1.

39. A blood pump arrangement according to claim 38, further comprising a drive motor, wherein a rotationally fixed and preferably axially displaceable connection exists between the drive motor and the coupling element of the drive shaft.

* * * * *

UNITED STATES PATENT AND TRADEMARK OFFICE
CERTIFICATE OF CORRECTION

PATENT NO. : 10,478,538 B2  
APPLICATION NO. : 15/033443  
DATED : November 19, 2019  
INVENTOR(S) : Scheckel et al.

Page 1 of 1

It is certified that error appears in the above-identified patent and that said Letters Patent is hereby corrected as shown below:

In the Specification

Column 3, Line 61, delete "MP35NO" and replace with --MP35N®--

Column 10, Line 23, delete "$A1_x$," and replace with --$AIO_x$,--

Signed and Sealed this  
Eleventh Day of February, 2020

Andrei Iancu  
*Director of the United States Patent and Trademark Office*